(12) United States Patent
Riley et al.

(10) Patent No.: US 7,147,876 B2
(45) Date of Patent: *Dec. 12, 2006

(54) COMPOSITIONS FOR REMOVAL OF TOXINS

(76) Inventors: Michael Hargreaves Riley, 26 Packhorse Road, Stratford-upon-Avon, Warwickshire (GB) CV37 9AW; Jane Clarissa Fletcher, 26 Packhorse Road, Stratford-upon-Avon, Warwickshire (GB) CV37 9AW ( * ) Notice: Subject to any disclaimer, the term of this patent is extended or adjusted under 35 U.S.C. 154(b) by 18 days.

This patent is subject to a terminal disclaimer.

(21) Appl. No.: 10/486,817

(22) PCT Filed: Aug. 5, 2002

(86) PCT No.: PCT/GB02/03590

§ 371 (c)(1),
(2), (4) Date: Apr. 15, 2004

(87) PCT Pub. No.: WO03/015805

PCT Pub. Date: Feb. 27, 2003

(65) Prior Publication Data

US 2004/0208941 A1  Oct. 21, 2004

(30) Foreign Application Priority Data

Aug. 13, 2001 (GB) ............... 0119723.5
Nov. 14, 2001 (GB) ............... 0127364.8

(51) Int. Cl.
*A61K 36/00* (2006.01)

(52) U.S. Cl. .................. 424/744; 424/725

(58) Field of Classification Search ........ 424/725, 424/744

See application file for complete search history.

(56) References Cited

U.S. PATENT DOCUMENTS

| | | | |
|---|---|---|---|
| 4,918,099 A | 4/1990 | Moon | |
| 5,073,545 A | 12/1991 | Arima et al. | |
| 5,356,811 A | 10/1994 | Coats | |
| 5,578,307 A | 11/1996 | Wunderlich et al. | |
| 6,190,678 B1 * | 2/2001 | Hasenoehrl et al. | 424/401 |
| 6,280,751 B1 * | 8/2001 | Fletcher et al. | 424/401 |

FOREIGN PATENT DOCUMENTS

| | | | |
|---|---|---|---|
| CN | 950110064 | | 9/1996 |
| FR | 2555445 | | 5/1985 |
| JP | 890073166 | | 10/1990 |
| JP | 950296579 | | 5/1997 |
| JP | 960332588 | | 7/1997 |
| JP | 2000143437 A | * | 5/2000 |
| RU | 925034304 | | 10/1993 |
| RU | 930007452 | | 10/1993 |
| RU | 930044640 | | 1/1996 |
| RU | 940021907 | | 3/1996 |
| RU | 940005006 | | 9/1996 |
| RU | 91 955645 | | 6/1997 |
| RU | 940025611 | | 7/1997 |
| RU | 940040946 | | 10/1997 |
| RU | 950107535 | | 10/1997 |
| SU | 86 154948 | | 3/1989 |
| WO | WO-93/11780 | | 6/1993 |

OTHER PUBLICATIONS

Internet website: www.beat-your-health-condition.com/benefits-of-tea-tree-oil.html. (2 pages total).*

* cited by examiner

*Primary Examiner*—Christopher Tate
*Assistant Examiner*—S. B. McCormick-Ewoldt
(74) *Attorney, Agent, or Firm*—Kilpatrick Stockton, LLP

(57) ABSTRACT

A medicinal or cosmetic composition comprising *Aloe vera* in combination with at least one vitamin, a minerals concentrate, an organic oils concentrate, at least one Chinese Herb, at least one essential oil and at least one spice. The composition may be administered orally or topically.

9 Claims, No Drawings

COMPOSITIONS FOR REMOVAL OF TOXINS

CROSS-REFERENCE TO RELATED APPLICATIONS

This application is the U.S. national phase of International Application No. PCT/GB02/03590 filed on Aug. 5, 2002 and published in English as International Publication No. WO 03/015805 A1 on Feb. 27, 2003, which application claims priority to Great Britain Application No. 0119723.5 filed on Aug. 13, 2001 and Great Britain Application No. 0127364.8 filed on Nov. 14, 2001, the contents of which are incorporated by reference herein.

The invention relates to medicinal and cosmetic compositions comprising an essential oil in combination with at least one spice and/or at least one herb. Such compositions may be taken orally or may be absorbed through the skin.

Essential oils have been used for thousands of years in aromatherapy. The ancient Chinese are generally acknowledged as the founders of aromatherapy, but it is more than likely that quite early in the history of civilisation man had realised that certain aromatic plants could help restore his health. Aromatic substances were also used by the ancient Egyptians and Ancient Greeks as medicinal perfumes.

In the 10th century the Arabs were extracting essential oils from aromatic plants and using them medicinally. The Knights of the Crusades brought aromatic essences and waters back to Europe from the Middle East and they became so popular that perfume began to be manufactured and was well established by the end of the 12th century. The importance of aromatic plants for other purposes was realised early. When the bubonic plague reached England around the middle of the 14th century, fires were ordered in the streets at night, burning aromatic frankincense and pine; indoors, incense and perfumed candles were burnt to combat infection and disguise the stench of death; pomanders made from aromatic gums and resins were worn on ribbons round the neck to protect the wearers from the dreaded Black Death.

By the turn of the 18th century essential oils were widely used in medicinal preparations and Salmon's dispensary of 1896 contains recipes for numerous aromatic remedies. In the 19th century, essential oils were subjected to more scientific investigation, and it was discovered that some of them could be synthesised from other materials. As it is always quicker and cheaper to produce the laboratory versions than natural plant extracts, true essential oils began to fall from favour. Today, many of our medicines and perfumes contain so-called essential oils, though often they are mere imitations; while synthetics may smell like the real thing, they do no possess the same therapeutic properties.

Essential Oils

Essential oils are highly scented droplets found in minute quantities in the flowers, stems, leaves, roots and barks of aromatic plants. They are not true oils in the manner of lubricant vegetable oils, but highly fluid and exceptionally volatile.

Essential oils are complex mixtures of different organic molecules—terpenes, alcohols, esters, aldehydes, ketones and phenols. Synthetic oils are usually made from one or more of the constituents predominant within a particular essential oil; menthol, for example, often substitutes for mint and eucalyptol for eucalyptus. However, there are sound reasons for believing that it is the interaction between each and every component that gives an essential oil its particular character and unique therapeutic properties.

The chemical composition of an oil is related to the time of day, the month or the season. Jasmine develops a strongly scented indole molecule at midnight when it is particularly intoxicating, and it is important to gather the petals at exactly the right moment. There are good years and bad years for essential oils as there are with wines. Some commercial producers have discovered that they can improve the quality of a poor yield by adding certain components and that an expensive oil like rosemary can be adulterated, without altering its aroma, by adding 30–40% of camphor which is considerably cheaper for the perfume industry. Such adulteration may be commercially acceptable but it might well alter the therapeutic properties of the oil. It is important to try to ensure that essential oils come from reputable sources and are as pure as possible.

Experts recognise an essential oil by its aroma and check its composition by a process called Gas Liquid Chromatography. Colour can also be an indicator; eucalyptus is colourless, chamomile varies from white to blue and others, like basil and sandalwood (both light greenish-yellow), are in pastel shades. Yet others are richly pigmented, like jasmine, a deep reddish-brown, patchouli, brown, and rose, orange-red.

Extraction of the Oils

Essential oils may be extracted from plants in a number of ways. One of the oldest methods is distillation, practised in ancient Persia, Turkey and India thousands of years ago. The Egyptians were preparing essence of cedarwoods for embalming and other purposes around 2000 BC; the wood was heated in a clay vessel covered by a screen of woollen fibres through which the steam had to pass. The essence was obtained by squeezing out the impregnated wool.

The Arabs are credited with having popularised distillation in the late 10th century. They began with extract of rose petals then experimented with other aromatic materials. Today, distillation remains the most commonly used means of extracting essential oils.

Other methods include enfleurage, often used for delicate petals like jasmine and tuberose; maceration, for tougher flowers and leaves, roots and bark; solvent extraction, the preferred method for gums and resins like myrrh and galbanum; and hand expression, chiefly employed for squeezing the highly aromatic oils from thick-skinned citrus fruit like oranges, tangerines and lemons.

The Properties and Uses of Essential Oils

Essential oils possess numerous properties which make them useful for treating many of our most common health and beauty troubles.

Professor Paolo Rovesti, Director of the Instituto Derivati Vegetali in Milan, has studied the effect of essential oils on the psyche and found that they can be useful in the treatment of anxiety and depression. He recommends ylang-ylang, citrus oils, jasmine, basil, patchouli and peppermint for treating general depression, geranium, lavender and bergamot for treating fear and anxiety, and peppermint, rose and carnation for improving concentration and eliminating lethargy. Sprayed into the air, these oils also have immediate and long-lasting effects.

The reasons for these reactions are as yet unclear, but it is known that odour molecules are perceived by thousands of tiny nerve cells in the nose and that each of these nerves is connected to that part of the brain which is concerned with emotional drives, creativity and sexual behaviour. This could explain why certain perfumes make us feel happy, why some essences, like jasmine and rose, have a reputation for being aphrodisiac and why unpleasant smells, like petrol fumes, can induce depression. While pure essential oils appear to have a positive influence on the psyche, it is doubtful that synthetic ones work in the same way.

Spices are conventionally used as flavourings in, for example, Indian or Thai dishes. Spices are usually the dried, aromatic parts of plants, generally the seeds, berries, roots, pods and sometimes leaves and flesh, which mainly, but not invariably, grow in hot countries.

The medicinal uses of spices in the past were often indistinguishable from their culinary uses, particularly so in mediaeval times, when apothecaries prescribed herbs and spices not merely for digestive problems, but for all types of ailments. Hot spices, such as pepper, were regarded as an appetite stimulant and a digestive aid; asafoetida, now known only in Indian cookery, was used by the Romans as a healing ointment, an antidote for snake bites, and an cure for gout, cramps, pleurisy, and tetanus; spiced salts were made with ginger, pepper, cumin, thyme and celery seed which were good for the digestion, promoting regularity and preventing all sorts of illnesses, plagues and chills; and citron seeds were given to pregnant women to relieve nausea. Roman and mediaeval writers also believed the fennel helped to promote and restore good vision and it was at one time a cure for obesity.

Chinese herbal medicine has been known in China for several thousands of years. Only recently, however, has it become recognised in the West that Chinese herbs may be used to treat medical conditions.

The inventors have unexpectedly found that it is possible to combine essential oils with naturally occurring spices and/or Chinese herbs to produce medicinal compositions which may be taken orally or which may be directly absorbed through the skin. Compositions of the invention may be used to treat a surprising range of illnesses.

Such compositions are especially important with the move by many members of the public towards more "natural" treatments, which do not use artificial medicines.

Accordingly a first aspect of the invention provides a medicinal or cosmetic composition comprising *Aloe vera* in combination with at least one Vitamin, at least one Chinese herb, at least one essential oil and at least one spice.

Preferably the composition comprises a minerals concentrate and/or an organic oils concentrate.

*Aloe vera* extract is the delivery vehicle for the other components of the composition. It is readily accepted by the body and has not been found to produce allergic reactions or side effects. Preferably the extract is concentrated, for example, in powder form. The extract may be purified by, for example, cold pressing. Such purification removes aloins which have laxative properties when taken internally. Preferably the whole leaf is used to obtain the extract. The full potency of the polysaccharides in the *Aloe vera* is preferably maintained.

Examples of vitamins include Vitamin C, Vitamin D, Vitamin E (Alpha Tocapherol), Grapeskin Polyphenol, Pycnogenol (French Maritime), Pine Bark Extract and Inositol.

In a first preferred embodiment, known as a Delivery and Bio Availability System, the compositions comprise one or more essential oils selected from:

(a) Alfalfa, Clove Buds, Tea Tree, Apricot Seed, Bergamot, Chamomile Bleu, Chamomile German, Chamomile Maroc, Chamomile Roman, Cinnamon Zeylanicium, Eucalyptus Globulus, Fennel, Frankincense, Hyssop, Juniper, Lemon Grass, Niaouli, Pineseed, Rose Geranium, Rosemary, Savoury, Tagestes, Thyme Red and Ylang Ylang.

More preferably the compositions comprise one or more essential oils selected from: Alfalfa, Clove Buds and Tea Tree.

By comprise we mean that the composition contains ingredients, not that it consists solely of them.

In an alternative embodiment known as a pollution irrigator, the compositions comprise one or more essential oils selected from: Apricot Seed, Bergamot, Chamomile Maroc, Cinnamon Zeylanicium, Eucalyptus Globulus, Frankincense, Pineseed, Rose Geranium and Tagestes.

The compositions in the Delivery and Bio Availability System preferably comprise one or more Chinese herbs selected from:

(b) Bao Shao, Epidmedium Spinosa, Gan Cao, Gan Tiang, Gui Zhi, Lei Wan, Man Ting Zi, Shu Chang Pu, Tian Men Dong, Wu Wei Zi, Yin Yang Huo, Zi Su Ye, Chen Pi, Fu Hai Shi, Huang Qin, Jing Jie, Qing Hao, Tu Si Zi, Xin Yi Hua, Yu Xing Cao and Yuan Zhi.

More preferably the compositions comprise one or more Chinese herbs selected from: Epimedium Spinosa, Gan Tiang, Lei Wan, Man Ting Zi, San Qi and Wu Wei Zi.

In an alternative pollution irrigator embodiment the compositions comprise one or more Chinese herbs selected from: Bai Guo, Bai Guo Ye, Chen Pi, Fu Hai Shi, Qing Hao and Yuan Zhi.

Preferably the Delivery and Bio Availability compositions comprise one or more spices selected from:

(c) Caraway, Cloves Ground, Indian Brandee, Cardomon Ground and Celery Seeds Ground.

More preferably the compositions comprise one or more spices selected from: Caraway and Cloves Ground In a second alternative embodiment known as a "pollution irrigator" the compositions comprise one or more spices selected from: Cardomon Ground and Celery Seeds Ground.

Preferably the composition comprises all of the oils, herbs and spices from lists (a), (b) and (c). This combination has been found to especially improve the effectiveness of the compositions.

The compositions may further comprise Flower remedies, especially Bach flower remedies. Preferably the compositions comprise one or more flower remedies selected from: Beech, Chicory, Honeysuckle and Sweet Chestnut. Such remedies are well known in the art.

The composition may comprise a honey product such as royal jelly or bee propolis. Royal jelly and bee propolis have been used for many years to treat a wide range of conditions and as nutrient supplements.

Indian brandee may also be incorporated with the composition. Indian brandee has been used for many years as to relieve flatulence and colic. Its main ingredients are rhubarb tincture, capiscum tincture, ethanol, cochineal and methyl hydroxybenzoate.

Compositions of the invention may be used in combination with alternative methods of treatment such as aromatherapy, Bach flowers therapy, reflexology, acupuncture and/or the Alexander technique, all of which are known in the art.

The first and second embodiments may be used independently or together.

The invention may be used orally. Accordingly the invention preferably provides tablets or capsules comprising the compositions of the invention for oral administration.

Another aspect of the invention provides the use of a medicinal composition according to the invention for the irrigation of the body, to remove toxins, and for the preparation of the body to receive further treatment.

The compositions of the invention may be used in conjunction with aromatherapy and/or reflexology and/or physiotherapy to produce enhanced results.

The invention further provides the use of a medicinal composition according to the invention in combination with a second composition comprising at least one essential oil in combination with at least one spice and/or herb.

Preferably the spice is an "Indian spice" as defined herein. The herb is preferably a "Chinese herb" as defined herein.

The composition may also comprise one or more flavourings, such as blackcurrant concentrate, vitamins, amino acids and minerals. Examples of vitamins include Vitamin A, Vitamin C and Vitamin D and Vitamin E, which may be in the form of alpha-tocopherol. Inositol, pepsin, selenium methionine, soya isolate, trace mineral clay, whey protein, zinc amino acid chelate and individual amino acids such as lysine may be used. Enzymes, such as plant extracts comprising enzymes may also be incorporated.

The essential oils, spices, Chinese herbs and vitamins preferably used within the second composition are shown in Tables 1 to 3. The tables also show the source or method of obtaining the component These are described in WO98/40086.

TABLE 1

| ESSENTIAL OILS |
| --- |
| Aniseed |
| Basil |
| Benzoin |
| Bergamot |
| Black Pepper |
| Camphor |
| Carrot |
| Cedarwood |
| Chamomile German |
| Chamomile Maroc |
| Chamomile Roman |
| Cinnamon Leaf |
| Clove Buds |
| Cypress |
| Dill |
| Eucalyptus Globulus |
| Fatigue |
| Fennel |
| Frankincense |
| Ginger |
| Grand Fir |
| Grapefruit |
| Grapeseed |
| Hazel |
| Hyssop |
| Jojoba |
| Juniper |
| Juniper Berry |
| Lavender |
| Lemon |
| Lemon Grass |
| Melissa |
| Mountain Savoury |
| Myrtle Red |
| Neroli |
| Niaouli |
| Patchouli |
| Peppermint |
| Pine |
| Red Myrtle |
| Rescue Remedy |
| Rose Geranium |
| Rosemary |
| Sandlewood |
| Spanish Marjoram |

TABLE 1-continued

| ESSENTIAL OILS |
| --- |
| Sweet Marjoram |
| Sweet Thyma |
| Tagestes |
| Tea Tree |
| Thyme Red |
| Thyme Sweet |
| Ylang Ylang |

TABLE 2

| SPICES |
| --- |
| Allspice |
| Allspice Ground |
| Anise Star |
| Aniseed |
| Arrowroot |
| Arrowroot Ground |
| Asafoetidia |
| Caraway Ground |
| Cardamom |
| Cardamom Seeds |
| Carob |
| Cassia |
| Cassia Bark |
| Cayenne Pepper |
| Celery Salt |
| Chilli |
| Chilli Powder |
| Cinnamon |
| Cinnamon Ground |
| Cinnamon Sugar |
| Cloves |
| Cloves Ground |
| Coconut Cream Block |
| Coconut Ground |
| Coconut Powder |
| Coriander |
| Coriander Ground |
| Cream of Tartar |
| Cumin |
| Dill |
| Dill Seeds |
| Dutch Caraway |
| Fennel |
| Fennel Powder |
| Fenugreek |
| Fenugreek Powder |
| Garlic |
| Ginger |
| Horseradish |
| Horseradish Ribbled |
| Juniper Berries |
| Laos |
| Laos Powder |
| Lemon Grass |
| Mace |
| Mace Ground |
| Mango Powder |
| Mixed Spices |
| Mixed Spices - Sweet |
| Mushroom |
| Mustard Seed Black |
| Mustard Seed Yellow |
| Nutmeg |
| Nutmeg Powder |
| Onion |
| Orris Root |
| Paprika - Sweet |
| Slippery Elm |
| Tamarind Block |
| Tumeric |

TABLE 3

HERBS

Ba Ji Tian
Bai Dou Kou
Bai Gou
Bai Guo Ye (Ginkgo)
Bai He
Bai Ji Tian
Bai Jiang Cao
Bai Zhi
Bai Zhu
Ban Xia
Bi Ji Tian
Bo He
Bladderwrack
Boswellia Serrata
Bu Gu Zhi
Cang Er Zi
Chai Hu
Chamaelirium Lurea (False Unicorn)
Chan Tiu
Che Qian Cao
Che Qien Zi
Che Quian Cao
Chen Xiang
Chi Shao Yao
Chuan Lian Zi
Da Huang
Da Zao
Dan Shen
Dang Gui (Dong Quai)
Dang Shen
Du Zhong
Echinacaea Angustifolia
Er Cha
Fan Xie Ye (Senna)
Fu Ling
Fu Pen Zi
Gao Ben
Garcinia Cambogia
Ge Gen
Gou Qi Zi (Lycium)
Gou Teng
Guaiacum Wood
Gui Ban
Guo Teng
Guo Ye (Ginkgo)
He Zi
Horsetail
Hu Huang Lian
Hu Po
Hua Jiao
Huai Jiao Zi
Huang Lian
Huang Qi
Huo Ma Ren
Ji Xue Feng
Jiang Can
Jie Geng
Jin Quian Cao
Jin Yin Hua
Jin Ying Zi
Lian Zi
Lian Zi (Red)
Long Yan Rou
Lu Jiao Shuang
Ma Dou Ling
Mai Men Dong
Mai Ya
Man Jing Zi
Mao Zhao Cao (Cats Claw)
Mate Leaf
Mexican Yam Root
Milk Thistle Seed
Mu Dan Pi
Mu Hu Die
Mu Li

TABLE 3-continued

HERBS

Mu Tong
Niu Bang Zi
Ou Jie
Qiang Huo
Rou Cong Rong
Salix Alba (White Willow)
Sang Ye
Shan Zha
Shen Jin Cao
Sheng Ma
Shiu Niu Jiao Si
Shu Di Huang
Spirulina
Su Mu
Su Zi (Zi Su Zi)
Suan Zao Ren
Tian Ma
Tian Nan Xing
Ting Li Zi
Wang Bu Liu Xing Guo
Wu Bei Zi
Wu Jia Pi
Wu Yao
Xian He Cao
Xing Ren
Yan Hu Suo
Yang Rong Wan
Ye Ju Hua
Ye Tu Hua
Yi Mu Cao
Yin Yang Huo
Yohimbe
Zhen Zhu Mu
Zhi Mu
Zhi Zi Preferably the second composition comprises one or more essential oils selected from:
 (d) bergamot, chamomile german, chamomile maroc, chamomile roman, cinnamon zeylanicum, clove buds, eucalyptus globulus, frankincense, fennel, hyssop, juniper, lemon grass, mountain savoury, niaouli, red thyme, rosemary, rose geranium, tagestes and ylang ylang.

The second composition may comprise one or more Chinese herbs selected from:
 (e) acacia catechu, acanthopanax gracilistylus, caesalpinia sappan and epimedium spinosa Preferably the second composition comprises one or more spices selected from:
 (f) asapoetidia, coconut, coriander, fenugreek and horseradish.

Preferably the composition comprises all of the oils, herbs and spices from lists (d), (e) and (f). This combination has been found to especially improve the effectiveness of the compositions.

Essential oils are typically extracted by steam distillation, expression (hard pressing) or maceration. Such techniques are well known in the art.

CHINESE HERBS

Herbs and Their Properties

In China the herbs used are gathered from the wild by hand. The best ones grow far from human habitation, and the herbalists who gather them will also be botanists, explorers, climbers and environmentalists. They need to be able to identify the relevant herb in all stages of its development, know where the finest ones grow, be able to get to the plants even when they grow in highly inaccessible places, know how much they can take without threatening a particular species, and always be on the look-out for new sources and new species.

They are mostly imported from Hong Kong, although some come from mainland China via Beijing and Shanghai. Increasingly, as China opens its doors to the West, better access will be granted for importing herbs.

Some herbalists import their herbs directly, while others purchase them from Chinese herbal cash and carry stores in the West or from mail order suppliers.

Examples of Chinese herbs which may be used in the invention are listed above.

Preservation

Once the herbs have been collected from the wild they need to be treated so that they will keep their essential qualities during storage. They are always washed and dried. The method of drying varies depending on the particular herb and what it is going to be used for. They may be sun-dried or dried in a clay oven, alone or with other herbs. Sometimes they are dried with minerals such as sulphur, which bleaches them and also acts as a preservative. Occasionally you may hear of herbs being treated. This means that, after drying, they are stir-fried with angelica and milk vetch to enhance their properties. Some may also be buried in the ground to absorb moisture, or cooked in a clay pot with rice wine or honey to increase their potency.

Cutting up Herbs

Before or after they have been dried, the herbs will need to be cut up using a herb chopper. When this is done depends on the herb and its eventual usage. There are several ways of cutting herbs. Large roots are often sliced across at 90 degrees, which gives them a round cross-section, while smaller ones are cut at an angle to give a larger surface area. Some herbs are chopped very finely and compressed into a cake.

Some herbs have to be ground to a powder and this is done using a mortar and pestle with a lid, to avoid the loss of powder during crushing.

Storage

Traditionally, herbs would be stored in clay pots after preservation and cutting up. The shape of the clay pots and whether they were covered or uncovered depended on the herbs. The Chinese have always used clay pots, because clay was the simplest and cheapest material to get hold of and also because, when glazed and therefore non-absorbent, it helped to keep the properties of the herbs intact.

Modern herbalists increasingly use glass jars and bottles for herb storage, but still rely on wooden drawers for the bulk of their stocks because this is the easiest and most convenient method of dispensing them. These drawers are rarely labelled, as the herbalist is completely familiar with their contents. Since the drawers are arranged according to meridians and properties it would be hard for the herbalist to make a mistake that would result in a herb of a totally different type being dispensed.

Freshness of Stocks

However the herbs are stored, herbalists will check them periodically for mould and other signs of decay.

Herbs may need to be retreated—that is, washed and boiled, redried and, where necessary, freshly treated with angelica again in the same way that fresh herbs are.

Weighing Herbs

The scales used for most Chinese herbs are accurate to within approximately 3 grams. The scales are used by holding one of the strings near the pan and adjusting the weight on the rod.

Metric weights have been used for convenience, but Chinese herbalists use Chinese weights. Their names and metric equivalents are given below.

1 fan = 0.3 grams approx
10 fan = 1 qin = 3 grams approx
10 qin = 1 lian = 30 grams approx
16 lian = 1 jin = 480 grams approx Whenever scales are used, the weight given is always that of the herb before any stir-frying which may be specified on the prescription. The herbs may be fried in honey, water or rice wine, or 'burned' until black in a red-hot wok. These treatments naturally change the weight of the herb, and it is not unknown for patients to weight their herbs afterwards and mistakenly complain that they have been short-changed by the herbalist.

Boiling and Steaming

As soon as possible after collection, the herbs are boiled in clay pots. These come in a variety of shapes and sizes much like Western saucepans. It used to be traditional to throw away all pots used in medicinal preparations on the Chinese New Year's Eve. But few herbalists in the West can afford to do this now, especially since some of the decorated pots are extremely expensive.

Steam pots are used a lot for medicinal foods. The ingredients are added to the pot, after which both lids are put on and fastened by a string which passes through the handles. The pot is then placed in a larger pot of boiling water. The herbs and other ingredients are gently cooked by the rising steam without losing any valuable elements which might otherwise be boiled out.

Properties of Commonly Used Chinese Herbs

In the following lists the Chinese name has been used, along with the botanical name and the Western common name where possible. (Some Chinese herbs are not native to the West and have no corresponding Western name so in these cases the literal English translation has often been included.) Most of the herbs described here can be used in their fresh state, but they can all be ordered as dried herbs. Dosages given are standard ones from which herbalists would raise or lower according to the individual. It is interesting to note that many of the Chinese names have suffixes denoting parts of the plant, for example: hua/flower; pi/cortex or peel; ren/seeds; ye/leaf; zi/fruit or seeds. The dosage refers to the total dose over the course duration.

Details of preferably used herbs follows:

Bái dóu kòu

Pharmaceutical name: Fructus Amomi Kravanh

Actions

Aromatically transforms dampness: used in damp warm-febrile diseases with such symptoms as a stifling sensation in the chest, lack of appetite, and a very greasy tongue coating.

Warms the middle burner and causes rebellious qi to descent: for vomiting due to cold from deficiency of the spleen and stomach, or stomach cold.

Promotes the movement of qi and transforms stagnation: for stagnant qi of the spleen or stomach with such symptoms as fullness in the chest or epigastrium with distension and lack of appetite.

Bái guo

Pharmaceutical name: Semen Ginkgo Bilobae

Actions

Expels phlegm and stops wheezing: for wheezing with coughing and copious sputum.

Eliminates dampness and stops discharge: for vaginal discharge and turbid urine. This herb is used both in cases of deficiency and damp-heat.

Stabilises the lower burner: for urinary frequency or incontinence, or spermatorrhea Bai hé

Pharmaceutical name: Bulbus Lilii

Actions

Moistens the lungs, clears heat, and stops cough: for dry lung or lung-heat coughs and sore throat.

Clears the heart and calms the spirit: for such symptoms as intractable low-grade fever, insomnia, restlessness, and irritability in the aftermath of a febrile disease, Also for palpitations brought on by insufficiency of qi and yin.

Bài jiàng cao

Pharmaceutical name: Herba cum Radice Patriniae

Actions

Clears heat, relieves toxicity, and expels pus: for either internal fire toxin disorders, such as intestinal abscess, or fire toxin surface sores and swellings. May be taken internally or applied topically.

Dispels blood stasis and stops pain: for pain and obstruction associated with heat-induced blood stasis especially in the abdomen and chest. Also for post partum pain, and more recently for postoperative pain.

Bái sháo

Pharmaceutical name: Radix Paeoniae Lactiflorae

Actions

Nourishes the blood and regulates the menses: for blood deficiency with such symptoms as menstrual dysfunction, vaginal discharge and uterine bleeding. This is a very commonly-used herb for treating women's disorders.

Calms and curbs the liver yang and alleviates pain: for such symptoms as flank, chest or abdominal pain from either constrained liver qi or disharmony between the liver and spleen. In general, this herb is used to "soften and comfort" the liver, stop painful spasms in the abdomen, stop cramping pain or spasms in the hands and feet, and alleviate abdominal pain associated with dysenteric disorders. It is also used for headache and dizziness due to ascendant liver yang.

Preserves the yin and adjusts the nutritive and protective levels: for vaginal discharge and spermatorrhea as well as exterior wind-cold from deficiency patterns with continuous sweating that does not resolve the problem. It is also used for yin deficiency where the yang floats to the surface causing spontaneous sweating or night sweats.

Baí zhi

Pharmaceutical name: Angelicae Dahuricae

Actions

Expels wind and alleviates pain: for patterns of externally-contracted wind-cold, especially those with headache. Also for supraorbital pain, nasal congestion, and toothache. While primarily a warming herb, it can be used for any problem due to wind invading the yang brightness channels of the head.

Reduces swelling and expels pus: for early stages of surface sores and carbuncles. If the sore, ulcer, or carbuncle has not yet suppurated, this herb will help reduce the swelling. If pus has already formed or the sore has ulcerated, the herb can be used to help discharge the pus.

Expels dampness and alleviates discharge: usually for vaginal discharge due to damp-cold in the lower burner, but with the appropriate herbs can also be used to treat vaginal discharge from damp-heat.

Opens up the nasal passages: for sinus congestion.

Bàn xià

Pharmaceutical name: Rhizoma Pinelliae Ternatae

Actions

Dries dampness, transforms phlegm, and causes rebellious qi to descend: for cough with copious sputum, as in conditions of phlegm-cold in the lungs. Especially effective in transforming phlegm due to dampness of the spleen.

Harmonises the stomach and stops vomiting: for lingering phlegm-dampness in the stomach that rebels upward, causing nausea and vomiting.

Dissipates nodules and reduces distension: for modules, pressure, distension, or pain due to phlegm lingering in the chest, phlegm nodules in the neck )such as those of goiter and scrofula) or obstructions caused by phlegm anywhere in the body. Also for focal distension in the chest and epigastrium.

Bó hé

Pharmaceutical name: Herba Menthae Haplocalycis

Actions

Disperses wind-heat: for patterns of wind-heat with fever, headache, and cough.

Clears the head and eyes and benefits the throat: for patterns of wind-heat with sore throat, red eyes, and headache.

Vents rashes: used in the early stages of rashes (such as measles) to induce the rash to come to the surface and thereby speed recovery.

Allows constrained liver qi to flow freely: for constrained liver qi with such symptoms as pressure in the chest or flanks, emotional instability, and gynaecological problems.

Bu gu zhì

Pharmaceutical name: Fructus Psoraleae Corylifoliae

Actions

Tonifies the kidneys and fortifies the yang: for kidney yang deficiency patterns with such symptoms as impotence, premature ejaculation, cold and painful lower back, or weak lower back and extremities.

Stabilises the essence and reserves urine: for enuresis, incontinence of urine, frequent urination, and spermatorrhea.

Tonifies and warms the spleen yang: for cold deficient spleen diarrhoea, borborygmus, and abdominal pain. Most appropriate those cases with both spleen and kidney deficiency.

Aids the kidneys to grasp the qi: for wheezing when the kidneys do not grasp the lung qi.

Recently used topically for alopecia, psoriasis, and vitiligo.

Cang er zi

Pharmaceutical name: Fructus Xanthii Sibirici

Actions

Disperses wind and dispels dampness: for wind-damp painful obstruction or skin disorders with itching.

Opens the nasal passages: for any nasal or sinus problem with a thick, viscous discharge and related headache.

Dispels exterior wind: as an auxiliary herb for exterior disorders with a splitting headache that radiates to the back of the neck.

Chái hú

Pharmaceutical name: Radix Bupleuri

Actions

Resolves lesser yang disorders and reduces fever: for alternating chills and fever accompanied by a bitter taste in the mouth, flank pain, irritability, vomiting, and a stifling sensation in the chest associated with the lesser yang stage of externally-contracted disorders.

Spreads liver qi and relieves constraint: for constrained liver qi with such symptoms as dizziness, vertigo, chest and flank pain, emotional instability, or menstrual problems. Also used for disharmonies between the liver and the spleen with such symptoms as epigastric and flank pain, a stifling sensation in the chest, abdominal bloating, nausea, and indigestion.

Raises the yang qi in patterns of spleen or stomach deficiency: for haemorrhoids, anal or uterine prolapse, and diarrhoea due to collapse of the spleen qi.

Chán tuì

Pharmaceutical name: Periostracum Cicadae

Actions

Disperses wind and clears heat: for patterns of externally-contracted wind-heat, especially with loss of voice and a swollen, sore throat.

Vents rashes: for early stage of measles with an incomplete expression of the rash.

Clears the eyes and removes superficial visual obstruction: for wind-heat eye problems such as red, painful, and swollen eyes, or blurry vision Stops spasms and extinguishes wind: for childhood febrile diseases in which wind causes convulsions, spasms, delirium, or night terrors. Also used as an auxiliary substance in treating tetanus.

Chè qián zi

Pharmaceutical name: Semen Plantaginis

Actions

Promotes urination and clears heat: for any type of oedema or painful urinary dysfunction due to damp-heat. Generally used for damp-heat pouring into the lower burner.

Promotes urination to solidify the stool: for diarrhoea associated with either damp-heat or damp-summerheat.

Clears the eyes: for eye problems associated with either liver and kidney deficiency (e.g. dry eyes or cataracts) or heat in the liver channel (e.g. red, painful, swollen eyes and sensitivity to light) depending on which other herbs it is combined with.

Expels phlegm and stops cough: for lung heat-induced cough with copious sputum.

Chén pí

Pharmaceutical name: Pericarpium Citri Reticulatae

Actions

Regulates the qi, improves the transportive function of the spleen, adjusts the middle and relieves the diaphragm: for spleen or stomach stagnant qi patterns with such symptoms as epigastric or abdominal distension, fullness, bloating, belching, and nausea and vomiting. This herb promotes the movement of qi in general while specifically directing it downward. It is therefore commonly used in treating many different types of nausea and vomiting.

Dries dampness and transforms phlegm: an important herb for phlegm-damp coughs with a stifling sensation in the chest and/or diaphragm, and copious, viscous sputum. Also used for damp turbidity obstructing the middle with a stifling sensation in the chest, abdominal distension, loss of appetite, fatigue, loose stool and a thick, greasy tongue coating. An important qi-level herb of both the spleen and lung channels, it is especially appropriate for disorders involving both channels.

Helps prevent stagnation: used with tonifying herbs to prevent their cloying nature from causing stagnation.

Chén xiang

Pharmaceutical name: Lignum Aquilariae

Actions

Promotes the movement of qi and alleviates pain: for stagnant qi patterns with such symptoms as distension, pain or a feeling of pressure in the epigastric or abdominal region. Especially useful for problems due to cold from deficiency or blood stasis.

Directs rebellious qi downward and regulates the middle: for rebellious qi downward and regulates the middle: for rebellious qi wheezing of either the excessive or deficient type or vomiting, belching or hiccups due to cold from deficiency of the stomach or spleen.

Aids the kidneys in grasping the qi: for asthma and wheezing due to kidney deficiency.

Chì sháo

Pharmaceutical name: Radix Paeoniae Rubrae

Actions

Invigorates the blood and unblocks menstruation: for blood stasis patterns with amenorrhea, abdominal pain, post partum dizziness, lochioschesis and abdominal masses.

Dispels blood stasis and alleviates pain: for blood stasis wounds and pain, nonsuppurative sores, carbuncles and dark purplish erythema. Also for incomplete expression of the rash of measles or painful obstruction of the chest due to blood stasis.

Chuan liàn zi

Pharmaceutical name: Fructus Meliae Toosendan

Actions
- Promotes the movement of qi and stops pain: for flank, rib and abdominal pain due to constrained liver qi or liver-stomach disharmony. Also used for hernial disorders.
- Especially useful in cases with heat signs.
- Clears heat, dries dampness, regulates the qi and alleviates pain: for epigastric, abdominal, flank or hernial pain associated with damp-heat stagnant qi.
- Kills parasites and stops pain: for roundworms and tapeworms. Although this herb is not particularly effective in expelling parasites, it is able to alleviate pain and is therefore used for abdominal pain due to accumulation of parasites. Also used topically in powder form for tinea of the scalp.

Dà huáng

Pharmaceutical name: Radix et Rhizoma Rhei

Actions
- Drains heat and purges accumulations: for high fever, profuse sweating, thirst, constipation, abdominal distension and pain, delirium, yellow tongue coating and a full pulse. This presentation is referred to either as intestinal heat excess or the yang brightness organ-stage of the six stages of disease.
- Drains damp-heat: drains damp-heat via the stool, especially in cases of damp-heat jaundice or acute, hot dysenteric disorders. Also for painful urinary dysfunction.
- Drains heat from the blood: for blood in the stool either from bleeding haemorrhoids or heat accumulating in the intestines. Also for reckless movement of hot blood that overflows, manifested in vomiting blood or nosebleed accompanied by constipation.
- Invigorates the blood and dispels blood stasis: for amenorrhea, immobile abdominal masses, or fixed pain due to blood stasis. Also for blood stasis due to traumatic injury or intestinal abscess. This is an important herb for treating both recent and long-term blood stasis.
- Clears heat obstructing the blood level: for fever, hot, swollen and painful eyes or fire toxin sores due to heat excess obstructing the blood level.
- Clears heat and reduces fire toxicity: used either topically or internally for burns or hot skin lesions.

Dà zao

Pharmaceutical name: Fructus Zizyphi Jujubae

Actions
- Tonifies the spleen and augments the qi: for weakness, shortness of breath, lassitude, reduced appetite and loose stools due to spleen and stomach deficiency.
- Nourishes the blood and calms the spirit: for wan appearance, irritability and severe emotional lability due to restless organ disorder.
- Moderates and harmonises the harsh properties of other herbs.

Dan shèn

Pharmaceutical name: Radix Salviae Miltiorrhizae

Actions
- Invigorates the blood and breaks up blood stasis: For blood stasis disorders in the lower abdomen such as dysmenorrhea, amenorrhea, palpable masses, lochioschesis and pain due to blood stasis. It is also used for blood stasis obstructing the chest with chest or epigastric pain, as well as soreness in the ribs or hypochondria due to constrained liver qi with blood stasis.
- Clears heat and soothes irritability: especially useful for restlessness, irritability, palpitations and insomnia due to heat entering the nutritive level. It can also be used in patterns of heart and kidney yin deficiency.

Dang gui

Pharmaceutical name: Radix Angelicae Sinensis

Actions
- Tonifies the blood and regulates the menses: for patterns of blood deficiency with such symptoms as a pallid, ashen complexion, tinnitus, blurred vision and palpitations. Also very commonly used for blood deficiency associated with menstrual disorders such as irregular menstruation, amenorrhea, dysmenorrhea, etc.
- Invigorates and harmonises the blood and disperses cold: an important herb for stopping pain due to blood stasis. Commonly used for abdominal pain, traumatic injury and carbuncles due to blood stasis, especially when there is also cold from deficiency. Also used in the treatment of blood deficiency with chronic wind-damp painful obstruction.
- Moistens the intestines and unblocks the bowels: for dry intestines due to blood deficiency.
- Reduces swelling, expels pus, enerates flesh and alleviates pain: used in treating sores and abscesses where its ability to both tonify and invigorate the blood leads to improvement.

Dang shen

Pharmaceutical name: Radix Codonopsitis Pilosulae

Actions
- Tonifies the middle burner and augments the qi: for lack of appetite, fatigue, tired limbs, diarrhoea, vomiting or any chronic illness with spleen qi deficiency. Also for symptoms of prolapse of the uterus, stomach or rectum due to collapsed spleen qi.
- Tonifies the lungs: for lung deficiency with chronic cough and shortness of breath or copious sputum due to spleen qi deficiency.
- Strengthens the qi and nourishes fluids: for wasting and thirsting disorder or thirst due to injury to the fluids.
- Also used with herbs that release the exterior or drain downward when the presentation includes significant qi deficiency. In such cases, this herb "supports the normal" while the other herbs "expel the pathogenic influence".

Dù zhòng

Pharmaceutical name: Cortex Eurommiae Ulmoidis

Actions
- Tonifies the liver and kidneys, strengthens the sinews and bones: for liver and kidney deficiency with such symptoms as weak, sore or painful lower back and knees, fatigue and frequent urination.
- Aids in the smooth flow of qi and blood: used to promote circulation, especially in those with weakness of the sinews and bones.
- Calms the foetus: for cold deficient kidney patterns with bleeding during pregnancy. Also used to prevent miscarriage when the foetus is restless or agitated and when the pregnant woman has significant back pain or presents with a deficient condition.

Recently used for dizziness and lightheadedness (hypertension) from rising liver yang.

Ér chá

Pharmaceutical name: Pasta Acaciae seu Uncariae

Actions
Drains dampness and absorbs seepage: for sores that are filled with purulent fluid, chronic non-healing sores and sores of the oral cavity.
Stops bleeding: applied topically to stop bleeding due to external injuries.
Clears the lungs, transforms phlegm, generates fluids and stops diarrhoea: also taken internally for coughing due to lung heat, thirst due to summerheat, diarrhoea, bloody diarrhoea and dysenteric disorders. Such uses are now rare.

Fan xiè yè

Pharmaceutical name: Folium Sennae

Actions
Drains downward and guides out stagnation: for constipation due to heat accumulation in the intestines.

Fú hai shí

Pharmaceutical name: Pumice

Actions
Clears heat from the lungs and expels phlegm-heat: for heat accumulation in the lungs with sputum that is thick and difficult to expectorate, or with coughing up blood.
Softens hardness and dissipates phlegm nodules: for scrofula and similar disorders caused by phlegm-fire.
Promotes urination: for hot or stony painful urinary dysfunction.

Fú líng

Pharmaceutical name: Sclerotium Poriae Cocos

Actions
Promotes urination and leaches out dampness: for urinary difficulty, diarrhoea or oedema due to stagnation of fluids or dampness. Also used in cases of scanty urine due to damp-heat (more often in its red form).
Strengthens the spleen and harmonises the middle burner: for spleen deficiency compounded by dampness and such symptoms as loss of appetite, diarrhoea and epigastric distension.
Strengthens the spleen and transforms phlegm: for spleen deficiency with congested fluids in which phlegm moves upward with such symptoms as palpitations, headache, dizziness and a thick, greasy tongue coating.
Quiets the heart and calms the spirit: for palpitations, insomnia or forgetfulness.

Fù pén zi

Pharmaceutical name: Fructus Rubi Chingii

Actions
Augments and stabilises the kidneys, binds the essence and restrains urine: for urinary frequency or enuresis, spermatorrhea, premature ejaculation or wet dreams due to kidney yang deficiency.
Assists the yang and improves vision: for poor vision, sore lower back and impotence due to liver and kidney deficiency.

Gan cao

Pharmaceutical name: Radix Glycyrrhizae Uralensis

Actions
Tonifies the spleen and augments the qi: commonly used for spleen deficiency with shortness of breath, lassitude and loose stools. Also for qi or blood deficiency patterns with an irregular or intermittent pulse and/or palpitations.
Moistens the lungs and stops coughing: for coughing and wheezing. Because of its neutral properties, it can be used for either heat or cold in the lungs.
Clears heat and relieves fire toxicity: used raw for carbuncles, sores or sore throat due to fire toxin. For this purpose, it can be taken internally or applied topically.
Moderates spasms and alleviates pain: for painful spasms of the abdomen or legs.
Moderates and harmonises the characteristics of other herbs: by virtue of its sweet, neutral and moderating properties, this herb moderates hot and cold herbs and mitigates the violent properties of other herbs. Because it is said to enter all 12 primary channels, it can lead and conduct other herbs into the channels.
Also used as an antidote for a variety of toxic substances, both internally and topically.

Gan jiang

Pharmaceutical name: Rhizoma Zingiberis Officinalis

Actions
Warms the middle and expels cold: for warming the spleen and stomach both in conditions of excess due to externally-contracted cold, as well as cold from deficiency due to insufficiency of the yang qi.
Rescues devastated yang and expels interior cold: for devastated yang with such signs as a very weak pulse and cold limbs.
Warms the lungs and transforms phlegm: for lung cold with expectoration of thin, watery or white sputum.
Warms the channels and stops bleeding: for cold from deficiency that may present with haemorrhage of various types, especially uterine bleeding. It is used in treating haemorrhage only if the bleeding is chronic and pale in colour and is accompanied by cold limbs, ashen whit face and a soggy, thin pulse.

Gáo ben

Pharmaceutical name: Rhizoma et Radix Ligustici

Actions
Expels wind and alleviates pain: for externally-contracted wind-cold and especially for headache. Also for any wind pattern that presents with pain at the vertex or pain that travels from the vertex down to the cheeks and teeth. Also for acute lower back pain due to invasion of wind-cold, as it treats both ends of the governing vessel.

Gé gen

Pharmaceutical name: Radix Puerariae

Actions
Releases the muscles and clears heat: for exterior disorders lodged in the muscles manifesting in fever, headache and stiff or tight upper back and neck Nourishes the fluids and alleviates thirst: for thirst due to stomach heat. Especially appropriate in cases of externally-contracted heat.

Vents measles: to hasten recovery from measles with incomplete expression of the rash.

Alleviates diarrhoea: for diarrhoea or dysenterial disorders due to heat Can also be used for diarrhoea due to spleen deficiency when combined with other appropriate herbs.

Treats symptoms of hypertension: this herb has recently been used to treat the headache, dizziness, tinnitus or paresthesias that can accompany hypertension.

Gui ban

Pharmaceutical name: Plastrum Testudinis

Actions

Nourishes the yin and anchors the yang: for yin deficiency with ascendant yang with such symptoms as night sweats, dizziness, tinnitus and steaming bone disorder. Also for yin deficiency of the liver and kidneys that generates internal wind symptoms such as facial spasms and tremors of the hands and feet Benefits the kidneys and strengthens the bones: for kidney yin deficiency with such signs as soreness of the lower back, weakness in the legs, retarded skeletal development in children or failure of the fontanel to close.

Cools blood and stops uterine bleeding: for excessive menstruation or uterine bleeding caused by reckless movement of hot blood.

Nourishes the blood and tonifies the heart: for heart deficiency with anxiety, insomnia and forgetfulness. Also for non-healing sores and ulcerations.

Guì zhi

Pharmaceutical name: Ramulus Cinnamomi Cassiae

Actions

Adjusts the nutritive and protective qi levels: for exterior cold from deficiency patterns where sweating occurs without any improvement in the patient's condition.

Warms the channels and disperses cold: for wind-cold-damp painful obstruction in joints and limbs, especially the shoulders. Also for gynaecological problems, such as dysmenorrhea, caused by cold obstructing the blood.

Unblocks the yang and transforms the qi: for oedema due to accumulation of cold phlegm or weak movement of the yang qi.

Warms and facilitates the flow of yang qi in the chest: for palpitations due to obstruction to the flow of yang qi in the chest. This can be due to either stagnation or deficiency.

Warms and facilitates the flow in the blood vessels: for dysmennorrhea with or without abdominal masses.

He zi

Pharmaceutical name: Fructus Terminaliae Chebulae

Actions

Binds up the intestines and stops diarrhoea: for chronic diarrhoea and dysenteric disorders. Can be used for both hot and cold patterns depending on the other herbs in the prescription.

Contains the leakage of lung qi, stop coughing and improves the condition of the throat: for chronic cough, wheezing and loss of voice. When combined with appropriate herbs, can be used for cough due to phlegm-fire obstructing the lungs.

Hú huáng lián

Pharmaceutical name: Rhizoma Picrorhizae

Actions

Drains damp-heat: for damp-heat dysenteric disorders or sores.

Clears heat from deficiency: for yin deficiency with heat signs.

Clears heat and reduces childhood nutritional impairment: most appropriate when this disorder is accompanied by abdominal distension, afternoon fevers and dysenteric diarrhoea.

Hu pò

Pharmaceutical name: Succinum

Actions

Arrests tremors and palpitations and calms the spirit: for palpitations with anxiety, excessive dreams, insomnia, forgetfulness, anxiety and seizures due to disturbance of the spirit. Also used for childhood convulsions and seizures.

Invigorates the blood and dissipates stasis: for amenorrhea or pain associated with palpable immobile masses due to blood stasis. Also used recently in treating coronary heart disease.

Promotes urination and invigorates the blood: for urinary retention or painful urinary dysfunction, especially with bloody urine.

Reduces swelling and promotes healing: for sores, carbuncles and ulcerations of the skin. Also for swelling and pain of the scrotum or vulvular area.

Hua Jiao (Chuan jiao)

Pharmaceutical name: Pericarpium Zanthoxyli

Actions

Warms the middle burner, disperses cold and alleviates pain: for spleen or stomach cold from deficiency with such symptoms as cold and pain in the abdomen, vomiting and diarrhoea.

Kills parasites and alleviates abdominal pain: used as an auxiliary herb for abdominal pain due to roundworms.

Huáng lián

Pharmaceutical name: Rhizoma Coptidis

Actions

Drains fire and relieves toxicity: for heat with blazing fire with such symptoms as high fever, irritability, disorientation, delirium, red tongue and a rapid and full pulse. Also for excessive heat with toxicity with such symptoms as painful, red eyes and sore throat and for boils, carbuncles and abscesses.

Clears heat and drains dampness: for damp-heat in the stomach or intestines that presents with diarrhoea or dysenteric disorder. Also for vomiting and/or acid regurgitation due to stomach heat.

Clears heart fire: for irritability and insomnia due to lack of communication between the heart and kidneys.

Clears heat and stops bleeding: for nosebleed or blood in the urine, stool or vomit due to reckless movement of hot blood.

Drains stomach fire: for digestive dysfunction with bad breath and belching with a putrid odour.

Clears heat topically: used topically for red and painful eyes and ulcerations of the tongue and mouth.

Huǒ má rén

Pharmaceutical name: Semen Cannabis Sativae

Actions

Nourishes and moistens the intestines: for constipation in the elderly, in the aftermath of a febile disease, post partum and in cases of blood deficiency.

Nourishes the yin: mildly tonifies the yin and primarily used in cases of yin deficiency with constipation.

Clears heat and promotes healing of sores: as an auxiliary herb for sores and ulcerations, taken orally or applied topically.

Huáng qín

Pharmaceutical name: Radix Scutellariae Baicalensis

Actions

Clears heat and drains fire, especially from the upper burner: for heat patterns with high fever, irritability, thirst, cough and expectoration of thick, yellow sputum or hot sores and swellings. In treating the latter it can be applied topically or taken internally.

Clears heat and dries dampness: a major herb for damp-heat in the stomach or intestines, which manifests as diarrhoea or dysenteric disorder; damp warm-febrile disease which presents with fever, stifling sensation in the chest and thirst but inability to drink; or for damp-heat in the lower burner with painful urinary dysfunction. Used as an auxiliary herb for damp-heat jaundice.

Clears heat and stops bleeding: for excessive internal heat causing the blood to move recklessly. Symptoms include vomiting or coughing of blood, nosebleed and blood in the stool.

Clears heat and calms the foetus: pacifies the womb when the foetus is restless or kicking excessively due to heat.

Sedates ascendant liver yang: for such symptoms as headache, irritability, red eyes, flushed face and bitter taste in the mouth.

Jiang cán

Pharmaceutical name: Bombyx Batryticatus

Actions

Extinguishes wind and stops spasms and convulsions: for childhood convulsions or facial paralysis. Also used for seizures from either internal movement of liver wind or wind-phlegm-heat.

Expels wind and stops pain: for headache, red eyes and sore, swollen throat from either externally-contracted or liver wind. Also used for loss of voice.

Transforms phlegm and dissipates nodules: for phlegm-heat scrofula and other phlegm nodules.

Expels wind and stops itching: for itching skin lesions such as wind rash.

Jié geng

Pharmaceutical name: Radix Platycodi Grandiflori

Actions

Opens up and disseminates the lung qi and expels phlegm: for cough. When combined with other appropriate herbs, it can be used for both wind-cold and wind-heat coughs.

Promotes the discharge of pus: for expelling pus associated with lung abscess or throat abscess.

Benefits the throat: used in many cases of sore throat or loss of voice, especially in those caused by external heat, but also when the condition is due to other factors such as phlegm-heat or yin deficiency with heat signs.

Directs the effect of other herbs to the upper regions of the body.

Jīn qián cao

Pharmaceutical name: Herba Lysimachiae

Actions

Promotes urination, unblocks painful urinary dysfunction and expels stones: for various types of painful urinary dysfunction. It is a very important herb for treating stones in both the urinary and biliary tracts.

Clears damp-heat in the liver and gallblader: for jaundice and/or red, swollen eyes due to damp-heat.

Reduces toxicity and swelling: for snakebite, abscess and traumatic injury.

Jīn yín hua

Pharmaceutical name: Flos Lonicerae Japonicae

Actions

Clears heat and relieves fire toxicity: for hot, painful sores and swellings in various stages of development, especially of the breast, throat or eyes. Also for intestinal abscess.

Expels externally-contracted wind-heat: for the early stages of warm-febrile diseases with such symptoms as fever, slight sensitivity to wind, sore throat and headache. Also for externally-contracted summerheat Clears damp-heat from the lower burner: for damp-heat dysenteric disorder or painful urinary dysfunction.

Jīn ying zi

Pharmaceutical name: Fructus Rosae Laevigatae

Actions

Stabilises the kidneys and retains the essence: for spermatorrhea, urinary incontinence and vaginal discharge due to deficiency and instability of the lower burner. Its astringent and binding actions are also used for prolapsed rectum or uterus as well as excessive uterine bleeding.

Binds up the intestines and stops diarrhoea: for chronic diarrhoea and dysenteric disorders.

Jing jiè

Pharmaceutical name: Herba seu Flos Schizonepetae Tenuifoliae

Actions

Releases the exterior and expels wind: for exterior patterns of either wind-cold or wind-heat (depending on the herbs with which it is combined). Also for carbuncles or boils when they first erupt, especially when accompanied by chills and fever.

Vents rashes and alleviates itching: for the initial stage of measles and pruritic skin eruptions.

Stops bleeding: as an auxiliary herb for haemorrhage, e.g. blood in the stool or uterine bleeding.

Léi wán

Pharmaceutical name: Sclerotium Omphaliae Lapidescens

Actions

Kills parasites: primarily for tapeworms, but also used for hookworm and roundworm infestations.

Lián zi

Pharmaceutical name: Semen Nelumbinis Nuciferae

Actions
- Tonifies the spleen and stops diarrhoea: for spleen deficiency with chronic diarrhoea and loss of appetite. This herb both augments and binds and is thus very useful in these conditions.
- Tonifies the kidneys and stabilises the essence: for premature ejaculation and spermatorrhea due to unstable, deficient kidneys. Also used for excessive uterine bleeding and vaginal discharge.
- Nourishes the heart and calms the spirit: for palpitations with anxiety, deficiency irritability and insomnia Especially useful for problems due to lack of communication between the kidneys and the heart.

Lóng yan ròu

Pharmaceutical name: Arillus Euphoriae Longanae

Actions
- Tonifies and augments the heart and spleen, nourishes the blood and calms the spirit: for insomnia, heart palpitations, forgetfulness or dizziness due to heart and spleen deficiency. Commonly used for problems associated with an excess of pensiveness or overwork.

Ma dou líng

Pharmaceutical name: Fructus Aristolochiae

Actions
- Clears the lungs, transforms phlegm, stops coughing and calms wheezing: for coughing and wheezing due to either lung heat or lung deficiency accompanied by heat signs, as long as there is phlegm clogging the lungs.
- Recently used for hypertension when accompanied by lightheadedness and flushing.
- Also used for bleeding haemorrhoids.

Mài yá

Pharmaceutical name: Fructus Hordei Vulgaris

Actions
- Reduces food stagnation and strengthens the stomach: for poor digestion due to stagnation and accumulation of undigested starchy foods, as well as poorly digested milk in infants. Also for weak digestion and loss of appetite in cases of spleen deficiency.
- Inhibits lactation: for women who are discontinuing nursing, or for distended and painful breasts.
- Facilitates the smooth flow of liver qi: for constrained liver qi manifesting as a stifling sensation and distension in the epigastrium or ribs, belching and loss of appetite.

Màn jing zi

Pharmaceutical name: Fructus Viticis

Actions
- Disperses wind and clears heat: for externally-contracted wind-heat, especially when the major complaint is headache or eye pain.
- Clears and benefits the head and eyes: for liver channel wind-heat manifesting as excessive tearing, red, painful or swollen eyes, or spots in front of the eyes.
- Drains dampness and expels wind: as an auxiliary herb for wind-dampness in the limbs causing stiffness, numbness, cramping or heaviness.

Mù hú dié

Pharmaceutical name: Semen Oroxyli Indici

Actions
- Moistens the lungs and clears the voice: for cough, sore throat and hoarseness.
- Comforts the liver and regulates the qi: for flank and epigastric pain due to constrained qi.
- Also used topically to promote healing of ulcerated suppurative sores.

Mu lì

Pharmaceutical name: Concha Ostreae

Actions
- Settles and calms the spirit: for palpitations with anxiety, restlessness and insomnia.
- Benefits the yin and anchors the floating yang: for irritability, insomnia, dizziness, headache, tinnitus, blurred vision, bad temper or a red, flushed face due to yin deficiency with ascendant yang.
- Prevents leakage of fluids: for continuous sweating in patents with steaming bone disorder or in the aftermath of a warm-febrile disease. Also used as an astringent for spontaneous sweating, night sweats, nocturnal emissions, spermatorrhea or vaginal discharge and uterine bleeding due to deficiency.
- Softens harness and dissipates nodules: for various kinds of lumps in the neck such as scrofula and goiter.
- Absorbs acidity and alleviates pain: used in calcined form for excessive stomach pain with a sour taste in the mouth.

Mù tong

Pharmaceutical name: Caulis Mutong

Actions
- Promotes urination and drains heat from the heart via the small intestine: for such symptoms as irritability accompanied by sores of the mouth or tongue and scanty urine. Also used in treating damp-heat, painful urinary dysfunction, oedema and leg qi.
- Promotes lactation and unblocks the blood vessels: for insufficient lactation; less commonly for amenorrhea and for pain and stiffness of the joints.

Níu bàng zi

Pharmaceutical name: Fructus Arctii Lappae

Actions
- Disperses wind-heat and benefits the throat: for externally-contracted wind-heat patterns with such symptoms as fever, cough and a sore, red, swollen throat.
- Clears heat and relieves toxicity: for red swellings, carbuncles, erythemas, mumps and acute febrile maculopapular rashes.
- Vents rashes: for the early stages of measles when there is incomplete expression of the rash.
- Moistens intestines: for wind-heat constipation.

Ou jié

Pharmaceutical name: Nodus Nelumbinis Nuciferae Rhizomatis

Actions
- Stops bleeding: used for many types of bleeding because it is both an astringent and breaks up blood stasis. Most often used for bleeding associated with heat in the lungs or stomach with vomiting or coughing of blood. Also for chronic bleeding when combined with other appropriate substances.

Qiang huó

Pharmaceutical name: Rhizoma et Radix Notopterygii

Actions
  Releases the exterior and disperses cold: for exterior cold patterns with such symptoms as chills, fever, headache and body aches and pains. Most commonly used when accompanied by dampness with joint pain, a general feeling of heaviness, sleepiness or when there is pain in the occipital region.
  Unblocks painful obstruction and alleviates pain: for wind-cold-damp painful obstruction, especially in the upper limbs and back.
  Guides qi to the greater yang channel and governing vessel: to direct other herbs in a prescription to the areas served by these two channels.

Qing hao

Pharmaceutical name: Herba Artemisiae Annuae

Actions
  Clears summerheat: especially for summerheat with low fever, headache, dizziness and a stifling sensation in the chest.
  Clears fevers from deficiency: for fevers from either blood deficiency or as the sequelae of a febrile disease. Especially for unremitting fever or night fever and morning coolness with an absence of sweating.
  Cools blood and stops bleeding: for purpuric rashes or nosebleed due to heat in the blood.
  Checks malarial disorders and relieves heat: for the alternating fever and chills of malarial disorders.

Ròu cóng róng

Pharmaceutical name: Herba Cistanches Deserticolae

Actions
  Tonifies the kidneys and strengthens the yang: for deficient kidney yang patterns with such symptoms as impotence, spermatorrhea, urinary incontinence, posturinary dripping and cold pains in the lower back and knees.
  Warms the womb: for infertility, excessive uterine bleeding and vaginal discharge from cold deficient womb.
  Moistens the intestines and facilitates passage of stool: for constipation involving dry intestines from inadequate fluids, especially in the elderly but also in debilitated people or those with deficient blood or qi.

San qi

Pharmaceutical name: Radix Notoginseng

Actions
  Stops bleeding and transforms blood stasis: for internal and external bleeding including vomiting blood, nosebleed and blood in the urine or stool. Because this herb can stop bleeding without causing blood stasis, it is very widely used.
  Reduces swelling and alleviates pain: the herb of choice for traumatic injuries, used for swelling and pain due to falls, fractures, contusions and sprains. Effective in invigorating blood, it is used for chest and abdominal pain, as well as joint pain that has been caused by blood stasis.

Sang yè

Pharmaceutical name: Folium Mori Albae

Actions
  Expels wind and clears heat from the lungs: for externally-contracted wind-heat with fever, headache, sore throat and coughing. Also for lung dryness with cough and dry mouth or lung heat with thick, yellow sputum.
  Clears the liver and the eyes: for liver channel eye problems due to either wind-heat or yin deficiency. Common symptoms include red, sore, dry or painful eyes, or spots in front of the eyes.
  Cools the blood and stops bleeding: for mild cases of vomiting of blood due to heat in the blood.

Shan zha

Pharmaceutical name: Fructus Crataegi

Actions
  Reduces and guides out food stagnation: for accumulation due to meat or greasy foods with accompanying symptoms of abdominal distension, pain or diarrhoea.
  Transforms blood stasis and dissipates clumps: for post partum abdominal pain and clumps due to blood stasis. Also for hernial disorders.
  Stops diarrhoea: the partially charred herb is used for the diarrhoea of chronic dysentery-like disorders.
  Also used recently for hypertension, coronary artery disease and elevated serum cholesterol.

Sheng má

Pharmaceutical name: Rhizoma Cimicifugae

Actions
  Releases the exterior and vents measles: for headache due to exterior wind-heat or the early stages of measles.
  Clears heat and relieves toxicity: for various manifestations of fire toxin in the upper or superficial aspects of the body. It is commonly used for sore teeth, swollen or painful gums, ulcerated lips or gums, canker sores, painful and swollen throat, sores or blotches from warm-febrile diseases.
  Raises the yang and lifts the sunken: for middle qi deficiency leading to such symptoms as shortness of breath, fatigue and prolapse. Also used as a messenger to guide the effects of other herbs upward.

Shí chang pu

Pharmaceutical name: Rhizoma Acori Graminei

Actions
  Opens the orifices, vaporises phlegm and quiets the spirit: for phlegm veiling and blocking the sensory orifices with such symptoms as deafness, dizziness, forgetfulness and dulled sensorium, as well as seizures or stupor.
  Harmonises the middle burner and transforms turbid dampness: for such symptoms as chest and epigastric fullness and abdominal pain due to dampness distressing the spleen and stomach.
  Also used both internally and topically for wind-cold-damp painful obstruction, trauma and sores.

Su mù

Pharmaceutical name: Lignum Sappan

Actions
  Invigorates blood, reduces swellings and alleviates pain: for blood stasis patterns such as post partum abdominal pain, amenorrhea or pain and swelling from falls, fractures, contusions or sprains.

Stops bleeding: for excessive post partum bleeding with dizziness, vertigo and shortness of breath.

Su zi

Pharmaceutical name: Fructus Perillae Frutescentis

Actions

Stops coughing and wheezing, redirects the qi downward and dissolves phlegm: for coughing and wheezing with copious phlegm. Especially useful when exhalation is more laboured than inhalation and there is a stifling sensation in the chest Moistens the intestines: for constipation due to dry intestines.

Suan zao rén

Pharmaceutical name: Semen Zizyphi Spinosae

Actions

Nourishes the heart yin, augments the liver blood and quiets the spirit: for irritability, insomnia and palpitations with anxiety due to either blood deficiency (inability to nourish the heart) or yin deficiency (with upward-rising fire).

Prevents abnormal sweating: for both spontaneous sweating and night sweats.

Tian mén dong

Pharmaceutical name: Tuber Asparagi Cochinchinensis

Actions

Nourishes kidney yin and clears lung heat: for yin deficiency with heat signs in the upper burner, typically dryness of the mouth. Also for dry lung patterns with such signs as dry mouth and thick or blood-streaked sputum that is difficult to expectorate.

Moistens the lungs, nourishes the kidneys and generates fluids: for lung and kidney yin deficiency especially wasting and thirsting disorder and consumption with low-grade afternoon fever. Also for constipation due to dry intestines.

Tian nán xing

Pharmaceutical name: Rhizoma Arisaematis

Actions

Dries dampness and expels phlegm: for cough and a stifling and distended sensation in the chest due to stubborn phlegm. This herb is extremely drying in nature.

Disperses wind-phlegm in the channels and stops spasms: for disorders in which wind and phlegm obstruct the channels causing dizziness, numbness in the limbs, facial paralysis, spasms in the hands or feet, opisthotonos, stroke, seizures or lockjaw.

Reduces swelling and alleviates pain: used topically for such problems as deep-rooted sores, ulcers and carbuncles. Also for swelling due to traumatic injury.

Tíng lì zì

Pharmaceutical name: Semen Descurainiae seu Lepidii

Actions

Drains the lungs, reduces phlegm and calms wheezing: for excess-type wheezing or coughing with copious sputum and a gurgling sound in the throat due to phlegm accumulation or lung heat.

Moves water and reduces oedema: for facial oedema or fluid accumulation in the chest or abdomen with urinary difficulty due to excess-type obstruction of the lung and bladder qi.

Tù si zi

Pharmaceutical name: Semen Cuscutae Chinensis

Actions

Tonifies the kidneys, augments the yin, secures the essence and reserves the urine: for deficient kidney yang patterns with such symptoms as impotence, nocturnal emission, premature ejaculation, tinnitus, frequent urination, sore painful back or vaginal discharge.

Tonifies the kidneys and liver and improves vision: for patterns of deficient liver and kidney yin and yang (e.g. deficient essence) with such symptoms as dizziness, tinnitus, blurred vision, or spots in front of the eyes.

Benefits the spleen and kidneys and stops diarrhoea: for diarrhoea or loose stools with a lack of appetite from deficiency of both the spleen and kidneys.

Calms the foetus: an important herb for habitual or threatened miscarriage.

Wu bèi zi

Pharmaceutical name: Galla Rhois Chinensis

Actions

Contains the leakage of lung qi and stops cough: for chronic cough due to lung deficiency.

Binds up the intestines and stops diarrhoea: for chronic diarrhoea, dysenteric disorders, chronic blood in the stool and rectal prolapse.

Preserves and restrains: for a wide variety of leakage problems including nocturnal emissions and spermatorrhea, excessive sweating and bleeding.

Absorbs moisture, reduces swellings and relieves fire toxicity: used topically as a powder or wash for such symptoms as sores, ringworm, toxic swellings and damp and ulcerated skin.

Also used topically for scar tissue.

Wu jia pí

Pharmaceutical name: Cortex Acanthopanacis

Actions

Dispels wind-dampness and strengthens the sinews and bones: for chronic wind-cold-damp painful obstruction when chronic deficiency of the liver and kidneys generates weak or soft sinews and bones. This herb is especially useful when the smooth flow of qi and blood is obstructed. It is particularly suitable for treating the elderly and for developmental delays in the motor functions of children.

Transforms dampness and reduces swelling: for urinary difficulty, oedema and damp-cold leg qi.

Wu wèi zi

Pharmaceutical name: Fructus Schisandrae Chinensis

Actions

Contains the leakage of lung qi and stops coughing: for chronic cough and wheezing due to lung deficiency or patterns of lung and kidney deficiency. This herb inhibits the leakage of lung qi above, enriching the kidney yin below, and also stops coughing. As such, it is an important and effective herb for chronic coughs.

Tonifies the kidneys, binds up essence and stops diarrhoea: for nocturnal emission, spermatorrhea, vaginal discharge and urinary frequency due to kidney deficiency. Also used for daybreak diarrhoea due to spleen and kidney deficiency.

Inhibits sweating and generates fluids: for excessive sweating, especially when accompanied by thirst or a dry throat. Depending on the other ingredients in the formula, it can be used for spontaneous sweating, night sweats or even wasting and thirsting disorders.

Quiets the spirit and calms the heart: for irritability, palpitations, dream-disturbed sleep and insomnia due to injury to the blood and yin of the heart and kidneys.

Recently used for allergic skin disorders and to improve liver function in patients with hepatitis.

Wu yào

Pharmaceutical name: Radix Linderae Strychnifoliae

Actions

Promotes the movement of qi and alleviates pain: for a stifling sensation in the chest, flank pain and epigastric and abdominal pain and distension due to cold constraint and qi stagnation. The herb warms and disperses and is effective in spreading and unblocking the qi mechanisms. It thereby smoothens the flow of qi, facilitates the middle, disperses cold and stops pain in many areas. It is also used when cold accumulation and qi stagnation manifest in lower abdominal pain, hernial disorder or menstrual pain.

Warms the kidneys: for frequent urination or urinary incontinence due to insufficiency of kidney yang and cold from deficiency of the bladder.

Xian hè cao

Pharmaceutical name: Herba Agrimoniae Pilosae

Actions

Restrains leakage of blood and stops bleeding: widely used for various types of bleeding such as vomiting blood, coughing of blood, nosebleed, bleeding gums, blood in the urine or uterine bleeding. Depending on its particular combination with other herbs, this herb can be used for bleeding due to heat, cold, excess or deficiency.

Alleviates diarrhoea and dysenteric disorders: for chronic problems, as this herb has a restraining nature.

Kills parasites: for trichomonas vaginitis and tapeworm.

Xin yí hua

Pharmaceutical name: Flos Magnoliae

Actions

Expels wind-cold and unblocks the nasal passages: for nasal obstruction or congestion, nasal discharge, loss of sense of smell, sinus problems, or related headache. While primarily used for problems due to wind-cold, it can also be used for any nasal or sinus condition, depending on the other herbs in the prescription.

Xing rén

Pharmaceutical name: Semen Pruni Armeniacae

Actions

Stops coughing and calms wheezing: used quite broadly for many kinds of cough disorders caused by either heat or cold, depending on the combination. Because the herb is moist in nature, it is especially useful for externally-contracted dry cough.

Moistens the intestines and unblocks the bowels: this secondary use of the herb derives from its high oil content.

Yán hú suo

Pharmaceutical name: Rhizoma Corydalis Yanhusuo

Actions

Invigorates the blood and alleviates pain: for pain due to blood stasis and traumatic injury. Especially useful for dysmenorrhea.

Promotes the movement of qi and alleviates pain: for stagnant qi that manifests with such symptoms as chest pain, abdominal pain, menstrual pain, hernial disorders and especially epigastric pain.

Ye jú hua

Pharmaceutical name: Flos Chrysanthemi Indici

Actions

Drains fire and relieves toxicity: for furuncles, carbuncles and sores. Also for sore, swollen throats and wind-fire causing red eyes.

Yì mu cao

Pharmaceutical name: Herba Leonuri Heterophylli

Actions

Invigorates the blood and regulates the menses: commonly used for gynaecological disorders such as irregular menstruation, pre-menstrual abdominal pain, immobile abdominal masses, infertility and post partum abdominal pain with lochioschesis.

Invigorates the blood and reduces masses: for abdominal masses or infertility caused by stasis from blood deficiency.

Promotes urination and reduces swelling: for acute systemic oedema. Especially useful for that which is accompanied by blood in the urine.

Yín yáng huò

Pharmaceutical name: Herba Epimedii

Actions

Tonifies the kidneys and fortifies the yang: for deficient kidney yang patterns with such symptoms as impotence, spermatorrhea, frequent urination, forgetfulness, withdrawal and painful cold lower back and knees.

Expels wind-damp-cold: for wind-damp-cold painful obstruction with such symptoms as spasms or cramps in the hands and feet, joint pain and numbness in the extremities.

Tonifies the yin and yang and harnesses ascendant liver yang: for lower back pain, dizziness and menstrual irregularity from deficient liver and kidneys and subsequent ascendant liver yang.

Yú xing cao

Pharmaceutical name: Herba cum Radice Houttuyniae Cordatae

Actions

Clears heat and toxin, reduces swellings and abscesses: for lung abscess or lung heat cough with expectoration of thick, yellow-green sputum.

Relieves toxicity and expels pus: for toxic sores, internally and topically.

Drains damp-heat and promotes urination: for large intestine damp-heat diarrhoea or damp-heat in the lower burner with painful urinary dysfunction.

Yuan zhì

Pharmaceutical name: Radix Polygalae Tenuifoliae

Actions
  Calms the spirit and quiets the heart: for insomnia, palpitations with anxiety, restlessness and disorientation. Most effective in cases related to excessive brooding or constrained, pent-up emotions.
  Expels phlegm and clears the orifices: used when phlegm envelops the orifices of the heart with such manifestations as emotional and mental disorientation or seizures.
  Expels phlegm from the lungs: for coughs with copious sputum, especially when difficult to expectorate.
  Reduces abscesses and dissipates swellings: for boils, abscesses, sores and swollen and painful breasts. Used in powdered form and applied topically or taken with wine.

Zhen zhu

Pharmaceutical name: Margarita

Actions
  Sedates the heart and settles tremors and palpitations: for palpitations, childhood convulsions and seizures. Also used for disharmony of the heart and spirit wherein the patient is easily frightened or angered.
  Clears the liver and eliminates superficial visual obstructions: for blurred vision due to pterygium or other superficial disorders of the eyes. Often used topically as a powder.
  Promotes healing and generates flesh: used topically as a powder for chronic, non-healing ulcers or macerated areas (usually throat or gums).

Zhi mu

Pharmaceutical name: Rhizoma Anemarrhenae Asphodeloidis

Actions
  Clears heat and drains fire: for high fever, irritability, thirst and a rapid, flooding pulse in patters of excessive heat in the lungs and stomach Also for cough due to heat in the lungs with expectoration of thick, yellow sputum.
  Enriches yin and moistens dry conditions: for exhaustion or deficiency of lung and kidney yin with heat signs such as night sweats, steaming bone disorder, irritability, afternoon or low-grade fevers, warmth in the five centres and bleeding gums. Also for such kidney heat signs as spermatorrhea, nocturnal emissions and abnormally elevated sexual drive.
  Generates fluids and clears heat: for oral ulcers and inflammation due to yin deficiency as well as wasting and thirsting disorder.

Zhi zi

Pharmaceutical name: Fructus Gardeniae Jasminoidis

Actions
  Clears heat and eliminates irritability: for heat patterns with fever, irritability, restlessness, a stifling sensation in the chest, insomnia or delirious speech.
  Drains damp-heat: for painful urinary dysfunction due to damp-heat in the lower burner; damp-heat and constrained liver and gallbladder (middle burner) with jaundice; and damp-heat in the gallbladder and triple burner channels of the face, affecting the nose and eyes or causing sores in the mouth or facial region.
  Cools the blood and stops bleeding: for heat in the blood with such symptoms as nosebleed, or blood in the vomit, stool or urine. For this purpose, the herb is partially charred.
  Reduces swelling and moves blood stasis due to trauma: for this purpose, apply topically as a powder mixed with egg white or vinegar.

Zi su yè

Pharmaceutical name: Folium Perillae Frutescentis

Actions
  Releases the exterior and disperses cold: for externally-contracted wind-cold with such symptoms as fever, chills, headache, nasal congestion or cough.
  Releases the exterior and disperses cold: for exterior disorders with headache and nasal congestion accompanied by cough or a stifling sensation in the chest.
  Promotes the movement of qi and expands the chest: for nausea, vomiting or poor appetite.
  Use during pregnancy: for calming a restless foetus or for morning sickness.
  Alleviates seafood poisoning: used either alone or with other herbs.

Preferably the minerals contain one or more minerals, especially in the form of a hydrophillic concentrate such as available from Rocklands Corporation, Tulsa, Okla., USA.

Especially preferred minerals include: calcium, phosphorous, sulphur, magnesium, copper, zinc, cobalt, chlorine, iron, iodine, manganese, zinc, molybdenum, selenium, chromium, and aluminium. These are preferably in the form of ionic salts.

The organic oils preferably contain one or more essential fatty acids and/or gamma linoleic acids. Preferably they contain omega 3 and omega 6 fatty acids. The fatty acids are preferably in a 1:1 ratio. The oils may be obtained commercially from, for example, Omega Nutrition, Vancouver, Canada. They may be a blend of one or more oils such as flax seed oil, sunflower/safflower oil, pumpkin oil and/or sesame oil.

The invention will now be described by way of example.

Typically the formulations comprise:
  $1/100$–1 ml., especially $1/10$ ml., each essential oil;
  1000–10000 mg., especially 2000 mg. to 8000 mg. each Chinese herb;
  1000–20000 mg., especially 4000 mg. to 10000 mg. each spice;
  0–30000 mg., especially 20000 mg. of each vitamin;
  5000–15000 mg., especially 10000 mg. Aloe vera;
  0–10 ml. flower remedies;
  0–50 ml., especially 20 ml. Indian Brandee;
  0–20000 mg. minerals; and
  0–20000 mg. organic oils concentrate.

The product formulae can be used in the treatment of a wide range of ailments. Typically the compositions are given in the form of capsules containing between 200 mg and 1 g of composition per capsule.

The formulations may also be taken neat or diluted with, for example 50% volume/volume cordial, fruit juice or lemonade.

The dosages may be separated into, for example, 3 equal doses taken after breakfast, lunch and an evening meal.

The *Aloe vera*, honey products, vitamins, minerals and organic oils are all commercially available products.

The *Aloe vera* products, heat lotion and propolis creme may be obtained from Forever Living Products (UK) Ltd, Longbridge Manor, Longbridge, Warwick, Warwickshire, United Kingdom. *Aloe vera* "juice" comprises as main ingredients stabilised *Aloe vera* gel, sorbitol, lemon juice, vitamin E, sodium benzoate and papain. "Pure" *Aloe vera* typically comprises stabilised *Aloe vera* gel, sorbitol, citric acid, vitamin E, sodium benzoate and papain. *Aloe vera* "nectar" comprises raw *Aloe vera* gel, fructose, sorbitol, cranberry and apple juice concentrate, ascorbic acid, citric acid, potassium sorbate, sodium benzoate, xanthan gum, tocopherol and colourings. Cold pressed *Aloe vera* is especially preferred. Concentrate may also be used.

Heat lotion comprises stabilized *Aloe vera* gel, DI water, propylene glycol, stearic acid, glyceryl stearate, triethanolamine, eucalyptus oil, methyl salicylate, apricot kernel oil, sesame oil, cetyl alcohol, petrolatum, lanolin, jojaba oil, oleic acid, stearyl stearate, dioctyl adipate, octyl stearate, octyl palmitate, PEG-100 stearate, allantoin, mineral oil, lanolin alcohol, ascorbic acid, diazolidinyl urea, methylparaben and propylparaben.

Propolis creme comprises stabilised *Aloe vera* gel, glyceryl stearate (and) PEG-1-00 stearate, propylene glycol, cetyl alcohol, dioctyl adipate (and) octyl stearate (and) octyl palmitate, lanolin, sorbitol, allantoin, bee propolis extract, lanolin alcohol, dimethicone, mineral oil, imodazolidinyl, urea, vitamins A & E, comfrey extract, chamomile extract, triethanolamine, ascorbic acid, methylparaben, propylparaben, fragrance.

Initial results indicate that the specific essential oil and herb/spice combination of the invention provides effective compositions for medical and/or cosmetic use.

The preferred compositions comprise:

*Aloe vera*, preferable as a 8000 concentrate powder 200:1; optionally Bee propolis 5:1 and/or pine honey (cronycive); one or more vitamins such as Vitamin A, Vitamin C and pine bark extract, optionally with Vitamin D, Vitamin E, grapeskin polyphenol, inositol, germanium, grapefruit extract, bioflavansid compositions and pycnogenol; hydrophilic minerals concentrate and organic oils concentrate; together with at least one Chinese herb, essential oil and spice selected from list A and/or B.

| List A | |
|---|---|
| Chinese Herbs | |
| Bai Shae | S |
| Epimedium Spinosa | P |
| Gan Cao | S |
| Gan Tiang | P |
| Gui Zhi | S |
| LeiWan (Calvacin) | P |
| Man Ting Zi | P |
| San Qi (Tian Qi) | P |
| Shi Chang Pu | O |
| Tian Men Dong | S |
| Wu Wei Zi | P |
| Yin Yang Huo | O |
| Zi Su Ye | S |
| Essential Oils | |
| Alfalfa (Lucern) | P |
| Clove Buds | P |
| Tea Tree | P |

| -continued | |
|---|---|
| Spices | |
| Caraway | P |
| Cloves Ground | P |
| Indian Brandee | O |
| List B | |
| Chinese Herbs: 5:1 | |
| Bai Guo | P |
| Bai Guo Ye | P |
| Chen Pi | P |
| Fu Hai Shi | P |
| Huang Qin | S |
| Jing Jie | S |
| Qing Hao | P |
| Tu Si Zi | O |
| Xin Yi Hua | S |
| Yu Xing Cao | S |
| Yuan Zhi | P |
| Essential Oils: | |
| Apricot seed | P |
| Bergamot | P |
| Chamomile Bleu | S |
| Chamomile German | O |
| Chamomile Maroc | P |
| Chamomile Roman | S |
| Cinnamon Zeylanicum | P |
| Clove buds | P |
| Eucalyptus Globulus | P |
| Fennel | S |
| Frankincence | P |
| Hyssop | O |
| Juniper | S |
| Lemon grass | S |
| Niaouli | S |
| Pineseed | P |
| Rose geranium | P |
| Rosemary | S |
| Savoury | O |
| Tagestes | P |
| Thyme red | S |
| Ylang Ylang | O |
| Spices | |
| Cardomom ground | P |
| Celery seeds ground | P |

P indicates most preferred components;
S indicates less preferred, secondary components;
O indicates other optional components.

The components may be used together with flower remedies such as beech, chicory, honeysuckle and sweet chestnut.

The Delivery and Bio Availability System has been shown by the inventors to improve the response of the body to the treatment of a variety of ailments, especially when used with other herbs and spices, such as those in WO 98/40086. It is thought that the formulation boosts the body's immune system.

The pollution irrigator is thought to improve the performance of such treatments by removing pollutants, herbicides, pesticides and other toxins from the body.

The invention claimed is:

1. A medicinal or cosmetic composition comprising *Aloe vera* in combination with Inositol, a minerals concentrate, an organic oils concentrate, Lei Wan, Tea Tree oil and Celery Seeds Ground.

2. A medicinal or cosmetic composition according to claim 1 wherein the composition further comprises one of more Vitamins selected from the group consisting of Vitamin C, Vitamin D, Vitamin E (Alpha Tocapherol), (Grapeskin Polyphenol, Pycnogenol (French Maritime) and Pine Bark Extract.

3. A medicinal or cosmetic composition according to claim 1 wherein the composition further comprises one of more Chinese herbs selected from the group consisting of Bao Shao, Epimedium Spinosa, Gan Cao, Gan Tiang, Gui Zhi, Man Ting Zi, Shu Chang Pu, Tian Men Dong, Wu Wei Zi, Yin Yang Huo, Zi Su Ye, Bai Guo, Bai Guo Ye, Chen Pi, Fu Hai Shi, Huang Qin, Jing Jie, Qing Hao, Tu Si Zi, Xin Yi Hua, Yu Xing Cao, and Yuan Zhi.

4. A medicinal or cosmetic composition according to claim 3 wherein the composition comprises one of more of Epimedium Spinosa, Gan Tiang, Man Ting Zi, San Qi and Wu WeiZi.

5. A medicinal or cosmetic composition according to claim 1 wherein the composition further comprises one of more essential oil selected from the group consisting of Alfalfa, Clove Buds, Apricot Seed, Bergamot, Chamomile Bleu, Chamomile German, Chamomile Maroc, Chamomile Roman, Cinnamon Zeylanicium, Eucalyptus Globulus, Fennel, Frankincense, Hyssop, Juniper, Lemon Grass, Niaouli, Pineseed, Rose Geranium, Rosemary, Savoury, Tagestes, Thyme Red and Ylang Ylang.

6. A medicinal or cosmetic composition according to claim 5 wherein the composition further comprises one of more of the following essential oils: Alfalfa and Clove Buds.

7. A medicinal or cosmetic composition according to claim 1 wherein the composition further comprises one of more spices selected from the group consisting of Caraway, Cloves Ground, Indian Brandee and Cardomon Ground.

8. A medicinal or cosmetic composition according to claim 7 wherein the composition comprises Cardomon Ground.

9. A medicinal or cosmetic composition comprises *Aloe Vera* in combination with Inositol, a minerals concentrate, an organic oil concentrate, Lei Wan, Tea Tree oil and Celery Seeds Ground;

wherein the composition is suitable for oral administration.

* * * * *